US00PP23365P3

(12) United States Plant Patent
Blom

(10) Patent No.: US PP23,365 P3
(45) Date of Patent: Jan. 29, 2013

(54) *CHRYSANTHEMUM* PLANT NAMED 'ZANMUBELLA'

(50) Latin Name: *Chrysanthemum×morifolium* Ramat
Varietal Denomination: Zanmubella

(75) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 11 days.

(21) Appl. No.: 12/923,737

(22) Filed: Oct. 6, 2010

(65) Prior Publication Data
US 2012/0090066 P1 Apr. 12, 2012

(51) Int. Cl.
*A01H 5/00* (2006.01)

(52) U.S. Cl. ..... Plt./296

(58) Field of Classification Search ..... Plt./286, Plt./287, 296
See application file for complete search history.

*Primary Examiner* — Susan McCormick Ewoldt
(74) *Attorney, Agent, or Firm* — Steptoe & Johnson LLP

(57) ABSTRACT

A *Chrysanthemum* plant named 'Zanmubella' characterized by its large sized blooms with bronze ray florets and prolific branching; and a response time of 8 weeks.

3 Drawing Sheets

Botanical designation: *Chrysanthemum×morifolium* Ramat.

Cultivar denomination: 'Zanmubella'.

BACKGROUND OF THE INVENTION

The present invention relates to a new and distinct cultivar of *Chrysanthemum* plant, botanically known as *Chrysanthemum×morifolium* Ramat., and hereinafter referred to by the cultivar denomination 'Zanmubella'. 'Zanmubella' is a product of a breeding and selection program for pot mums which had the objective of creating new cultivars with a double type inflorescence, a 8 weeks response and a medium plant height. 'Zanmubella' is a seedling resulting from a cross of the female parent id 9261 and the male parent id 17452. Plants of the new cultivar 'Zanmubella' differ from plants of the female parent in inflorescence color. The female parent has pink inflorescences, while 'Zanmubella' has bronze colored inflorescences. Plants of the new cultivar 'Zanmubella' differ from plants of the male parent in the following characteristics. (1). Plant vigor. And (2) Inflorescence color. (1). Plants of the male parent are less vigorous than those of 'Zanmubella'. (2). The inflorescences of the male parent are yellow.

The new and distinct cultivar was discovered and selected as a flowering plant within the progeny of the stated cross by Wilhelmus Bernardus Blom in a controlled environment (greenhouse) in Rijsenhout, The Netherlands in April 2004. The first act of asexual production of 'Zanmubella' was accomplished when vegetative cuttings were taken from the initial selection in June 2004 and propagated further in a controlled environment in Rijsenhout, The Netherlands. The new cultivar has been found to retain its distinctive characteristics through successive propagations, although the phenotype may somewhat vary with variations in environment such as light intensity and temperature.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
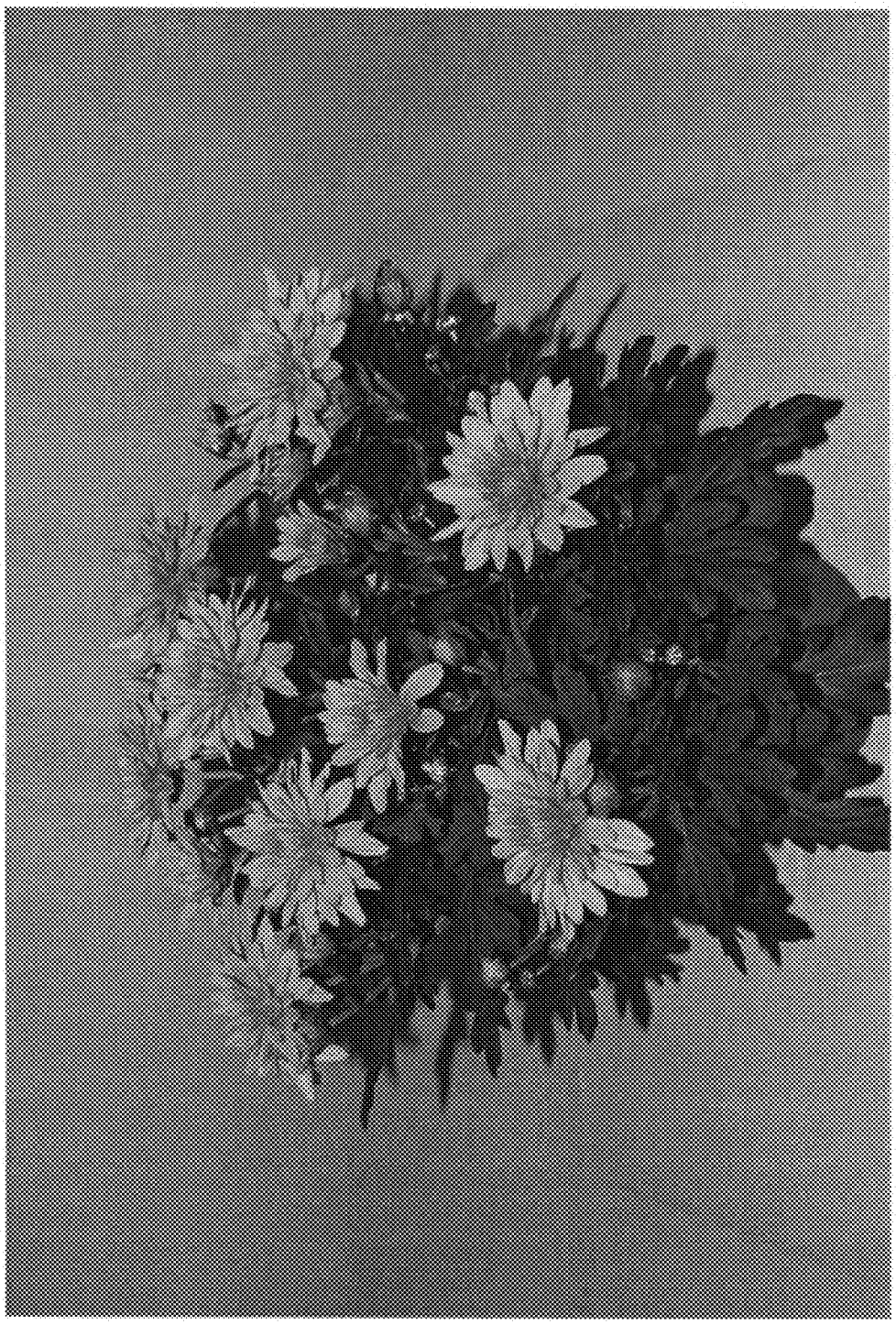
FIG. 1 shows a plant of the cultivar in full bloom.
Figure 2:
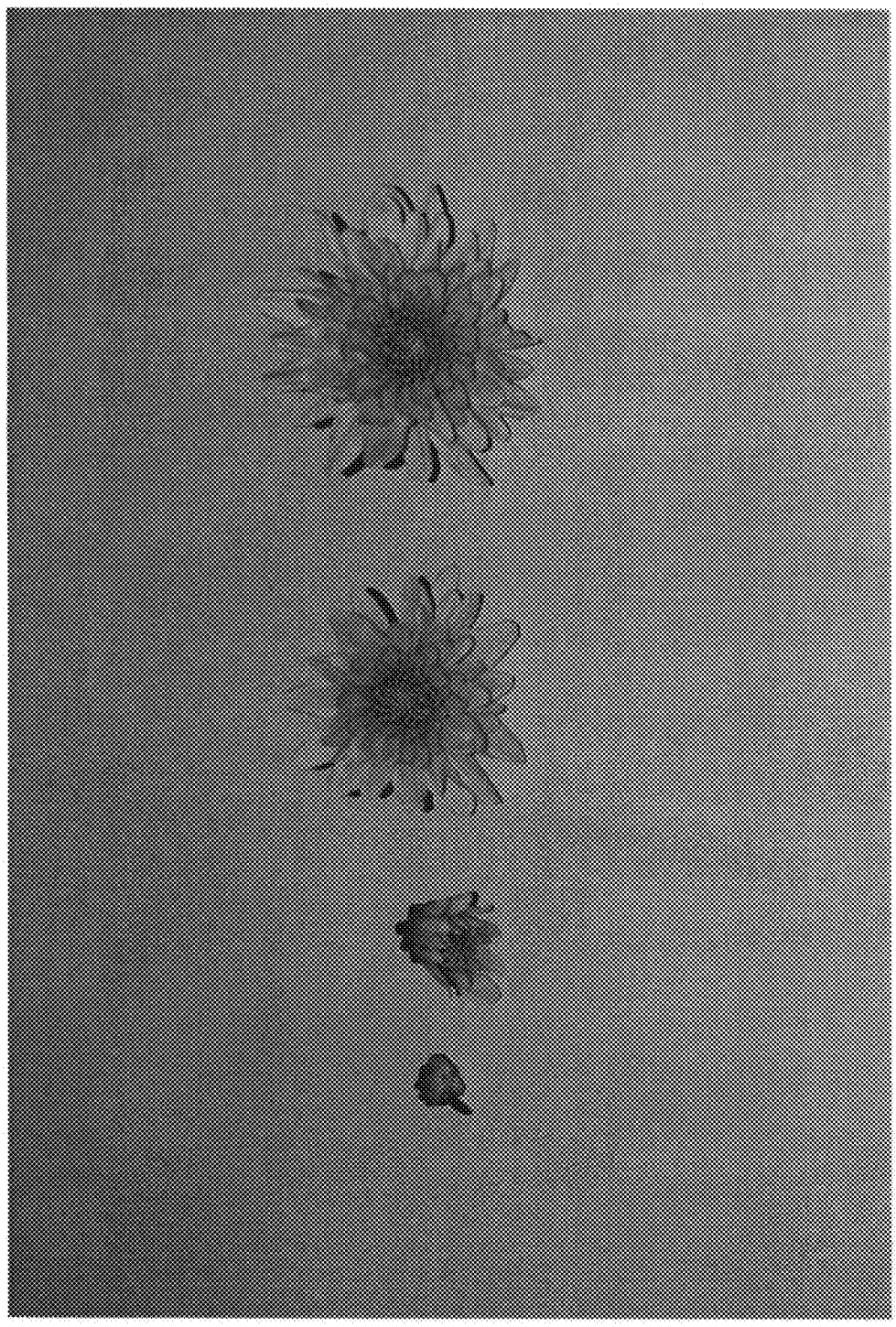
FIG. 2 shows the various stages of bloom of the new cultivar.
Figure 3:
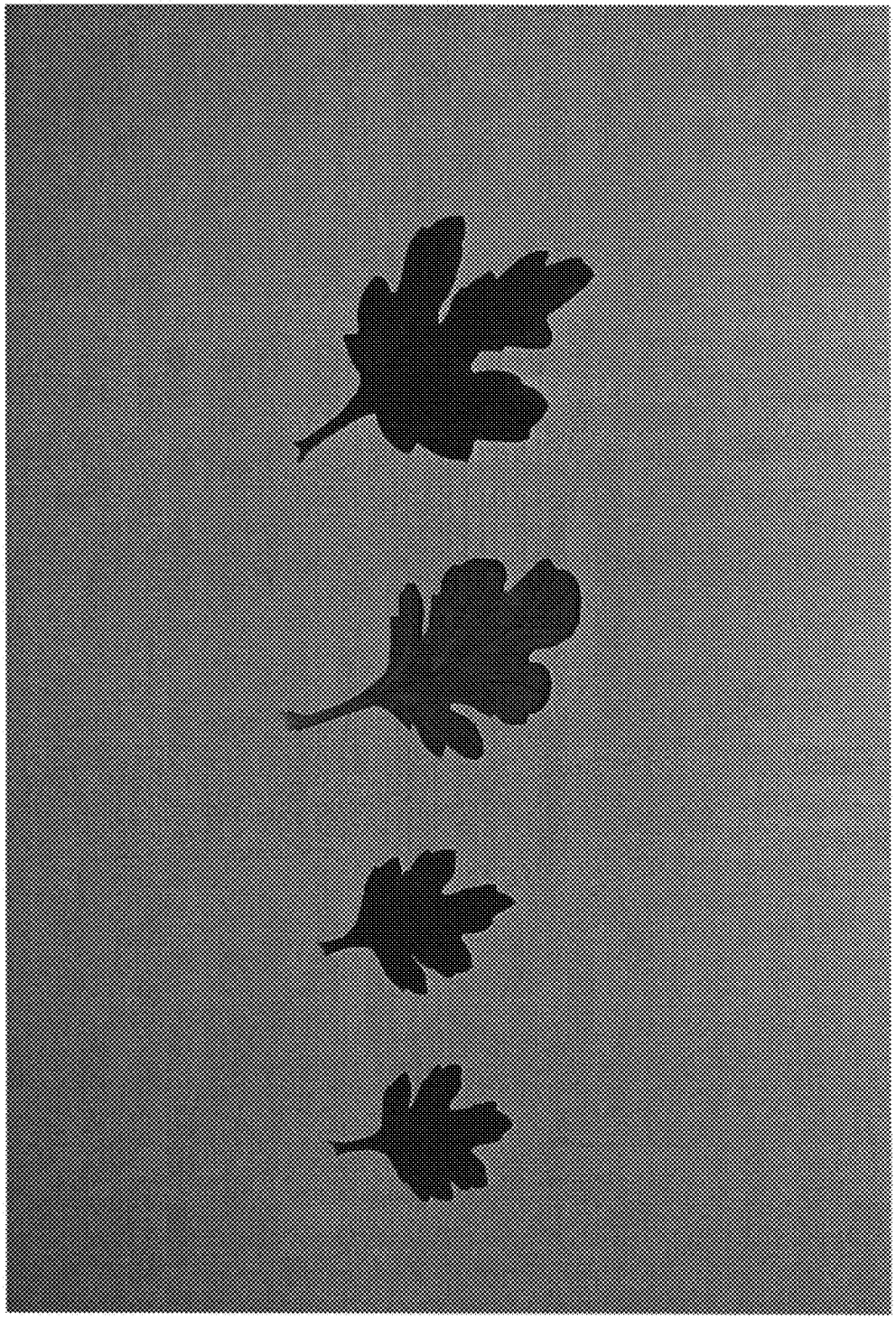
FIG. 3 shows the various stages of foliage of the new cultivar.

The observations and measurements were gathered in May 2010 from plants grown in a greenhouse in Rijsenhout, The Netherlands, in a photo-periodic controlled crop under conditions generally used in commercial practice. Five cuttings were planted in a pot with a diameter of 14 cm. The greenhouse temperatures for this crop were at day-time 18.degree. C. to 25.degree. C., and at night 20. Degree. C. The photoperiodic response time in this crop was 8 weeks after an average of eight long days. After this long day period growth retardants (Alar) were applied six times in an average dose of 1.5 gram/liter water until flowering. The plants were observed (directly) during the flowering of this crop. No tests were done on disease or insect resistance or susceptibility. No tests were done on cold or drought tolerance. To show the phenotype as described 'Zanmubella' can be planted without assimilation lighting (high pressure sodium lamps) between week 50 and week 40 of the next year under greenhouse conditions in the Netherlands. With assimilation lighting (minimum level 2500 lux) it can be planted all year round under greenhouse conditions in the Netherlands.

This new variety produces large sized blooms with bronze ray florets and a response time of 8 weeks.

From the cultivars known to inventor the most similar existing cultivar in comparison to 'Zanmubella' is 'Vamp Time Bronze' (U.S. Plant Pat. No. 15,710). When 'Vamp Time Bronze' and 'Zanmubella' are being compared the following difference is noticed: The difference of 'Vamp Time Bronze' and 'Zanmubella' are (1) Inflorescence size. And (2) Ray floret color. (1) The inflorescences of 'Vamp Time Bronze' are larger than those of 'Zanmubella'. (2) The ray florets of 'Vamp Time Bronze' are more orange colored than those of 'Zanmubella'.

The following is a description of the plant and characteristics that distinguish 'Zanmubella' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

DETAILED BOTANICAL DESCRIPTION

Bud:
- *Size*.—Medium; cross-section 7 mm, height 8 mm.
- *Shape*.—Round.
- *Texture*.—Smooth.
- *Outside color*.—Greyed-green 191A.

Phyllaries:
- *Number*.—14, arranged in 2 rows.
- *Shape*.—Elliptic.
- *Apex*.—Acute.
- *Base*.—Truncate.
- *Margin*.—Entire.
- *Color*.—Upper surface: Green 139B.
- *Length and width*.—8 mm; 2 mm.
- *Texture*.—Pubescent.

Inflorescence:
- *Type*.—Double.
- *Height*.—2.5 cm.
- *Diameter*.—6.5 cm.
- *Peduncle length*.—4.5 cm.
- *Peduncle color*.—Green 138B.
- *Peduncle diameter*.—1.5 mm.
- *Peduncle texture*.—Pubescent.
- *Number per branch*.—Approx. 4-5 inflorescences.
- *Shelf life bloom*.—4 weeks.
- *Seeds*.—None observed.
- *Fragrance*.—Faint *Chrysanthemum* odor.

Color:
- *Center of inflorescence*.—Immature stage: Yellow-green 150D. Mature stage: Greyed-Orange 164B.
- *Color of upper surface of the ray-florets*.—Greyed Orange 164B.
- *Color of the lower surface of the ray-florets*.—Greyed Orange 165D.
- *Tonality from distance*.—A pot mum with light bronze flowers.
- *Color of the ray-florets after aging of the plant*.—Greyed yellow 162B.

Ray florets:
- *Texture*.—Upper and lower side smooth.
- *Number*.—Ca. 150.
- *Shape*.—Elliptic.
- *Apex*.—Dentate.
- *Base*.—Acute.
- *Cross-section*.—Concave.
- *Longitudinal axis of majority*.—Straight.
- *Length of corolla tube*.—0.5 cm.
- *Ray-floret margin*.—*Entire*.
- *Ray-floret length*.—2.5-3.5 cm.
- *Ray-floret width*.—0.5-0.7 cm.
- *Ratio length/width*.—High.

Disc florets: Absent.

Receptacle:
- *Color*.—Yellow-green 145C.
- *Shape*.—Conical raised.
- *Height*.—0.4 cm.
- *Diameter*.—0.5 cm.

Reproductive organs:
- *Androecium*.—Absent.
- *Pollen*.—Absent.
- *Gynoecium*.—Present in ray florets.
- *Style color*.—Yellow-green 154C.
- *Style length*.—3 mm.
- *Stigma color*.—Yellow 7A.
- *Stigma width*.—1 mm.
- *Ovary*.—Enclosed in calyx.

Plant:
- *Form*.—Upright and free branching.
- *Growth rate*.—Medium.
- *Height*.—19 cm.
- *Width*.—30 cm.
- *Stem color*.—Greyed-brown 199A.
- *Stem strength*.—Strong.
- *Stem brittleness*.—Not brittle.
- *Stem anthocyanin coloration*.—Not observed.
- *Internode length*.—1-1.5 cm.
- *Length of lateral branch*.—From top to bottom 11 cm.
- *Lateral branch color*.—Green 137 C.
- *Lateral branch diameter*.—4 mm.
- *Lateral branch, attachment*.—Medium strength.
- *Branching* (*average number of lateral branches*).—Prolific with 4 breaks after branching.
- *Response time*.—8 weeks.

Foliage:
- *Leaf color*.—Upper surface: Green 139A. Lower surface: Green N138B.
- *Color midvein*.—Upper surface: Yellow-green 147D. Lower surface: Yellow-green 148D.
- *Size*.—Medium.; length 6-0 cm, width 3-5.5 cm.
- *Quantity* (*number per lateral branch*).—Ca. 12.
- *Shape*.—Broadly elliptic.
- *Texture upper side*.—Sparsely pubescent.
- *Texture under side*.—Pubescent.
- *Venation arrangement*.—Palmate.
- *Shape of the margin*.—Serrated.
- *Shape of base of sinus between lateral lobes*.—Rounded.
- *Margin of sinus between lateral lobes*.—Diverging.
- *Shape of base*.—Obtuse to truncate.
- *Apex*.—Mucronulate.
- *Petiole length*.—1.5-2.5 cm.
- *Petiole diameter*.—2-4 mm.
- *Petiole color*.—Yellow-green 147D.

TABLE 1

Differences with the comparison variety when grown side-to-side

| | 'Zanmubella' | 'Vamp Time Bronze' |
|---|---|---|
| Inflorescence diameter | 6. 5 cm | 8 cm |
| Ray floret color | Greyed Orange 164B | Greyed Orange 163B |

I claim:

1. A new and distinct *Chrysanthemum* plant named 'Zanmubella' as described and illustrated.

* * * * *